United States Patent
Ho et al.

(10) Patent No.: US 11,969,447 B2
(45) Date of Patent: *Apr. 30, 2024

(54) USE OF SPRAY-DRIED POWDER DERIVED FROM LACTIC ACID BACTERIAL STRAINS AND HERBAL EXTRACTS FOR PROMOTING DEFECATION

(71) Applicant: GLAC BIOTECH CO., LTD., Tainan (TW)

(72) Inventors: Hsieh-Hsun Ho, Tainan (TW); Ching-Wei Chen, Tainan (TW); Yi-Wei Kuo, Tainan (TW); Yu-Fen Huang, Tainan (TW); Cheng-Chi Lin, Tainan (TW)

(73) Assignee: GLAC BIOTECH CO., LTD., Tainan (TW)

( * ) Notice: Subject to any disclaimer, the term of this patent is extended or adjusted under 35 U.S.C. 154(b) by 0 days.

This patent is subject to a terminal disclaimer.

(21) Appl. No.: 17/204,245

(22) Filed: Mar. 17, 2021

(65) Prior Publication Data

US 2021/0401906 A1 Dec. 30, 2021

(30) Foreign Application Priority Data

Jun. 30, 2020 (TW) .................. 109121976

(51) Int. Cl.
| | | |
|---|---|---|
| A61K 36/82 | (2006.01) | |
| A23L 33/105 | (2016.01) | |
| A23L 33/135 | (2016.01) | |
| A61K 9/00 | (2006.01) | |
| A61K 35/745 | (2015.01) | |
| A61K 35/747 | (2015.01) | |
| A61K 36/185 | (2006.01) | |
| A61K 36/48 | (2006.01) | |
| A61K 36/736 | (2006.01) | |
| A61P 1/10 | (2006.01) | |
| A61K 35/00 | (2006.01) | |

(52) U.S. Cl.
CPC .......... *A61K 35/747* (2013.01); *A23L 33/105* (2016.08); *A23L 33/135* (2016.08); *A61K 9/0053* (2013.01); *A61K 35/745* (2013.01); *A61K 36/185* (2013.01); *A61K 36/48* (2013.01); *A61K 36/736* (2013.01); *A61P 1/10* (2018.01); *A23V 2002/00* (2013.01); *A23V 2400/113* (2023.08); *A23V 2400/181* (2023.08); *A23V 2400/515* (2023.08); *A23V 2400/531* (2023.08); *A61K 2035/115* (2013.01)

(58) Field of Classification Search
None
See application file for complete search history.

(56) References Cited

U.S. PATENT DOCUMENTS

| | | | | |
|---|---|---|---|---|
| 2019/0358273 A1* | 11/2019 | Hsieh | .................. | A61P 13/12 |
| 2021/0275612 A1* | 9/2021 | Liu | .................. | A23L 33/135 |
| 2021/0401907 A1* | 12/2021 | Ho | .................. | A61K 8/99 |
| 2021/0401908 A1* | 12/2021 | Ho | .................. | A61K 35/745 |

FOREIGN PATENT DOCUMENTS

| | | | |
|---|---|---|---|
| CN | 111150059 | * | 5/2020 |
| WO | WO 01/22934 | * | 4/2001 |

OTHER PUBLICATIONS

Hou, Y. et al. Origin and Concept of Medicine Food Homology and its Application in Modern Functional Foods. Food and Function 4:1727-1741, 2013. (Year: 2013).*

Khoshbakht K. et al. Savadhouh (Iran)—An Evolutionary Centre for Fruit Trees and Shrubs. Genetic Resources and Crop Evolution 53:641-651, 2006. (Year: 2006).*

Hsieh P. et al. Lactobacillus salivarius AP-32 and Lactobacillus reuteri GL-104 Decrease Glycemic Levels and Attenuate Diabetes . . . BMJ Open Diabetes Research and Care 8:1-9, Apr. 2020. (Year: 2020).*

Liu Y. et al. Bacteriostatic Activities of Lactic Acid Bacteria Against Extended Spectrum Beta Lactamase Producing *E. coli*. Basic Clinical Pharmacology Toxicology 125(Suppl S6)001, pp. 3-4, 2019. (Year: 2019).*

Berry Mom (https://mamibuy.com.bw.home/258062) The Best Digestion for the Whole Family Jan. 2019. (Year: 2019).*

* cited by examiner

*Primary Examiner* — Terry A McKelvey
*Assistant Examiner* — Catheryne Chen
(74) *Attorney, Agent, or Firm* — LAW OFFICES OF ALBERT WAI-KIT CHAN, PLLC

(57) ABSTRACT

A composition for promoting defecation includes a cell culture of at least one lactic acid bacterial strain which is substantially free of cells. The least one lactic acid bacterial strain is selected from the group consisting of *Lactobacillus salivarius* subsp. *salicinius* AP-32, *Bifidobacterium animalis* subsp. *lactis* CP-9, and *Lactobacillus acidophilus* TYCA06, which are respectively deposited at the Bioresource Collection and Research Center (BCRC) under accession numbers BCRC 910437, BCRC 910645 and BCRC 910813. Also disclosed is a method for promoting defecation, including administering to a subject in need thereof an effective amount of the composition.

9 Claims, 1 Drawing Sheet

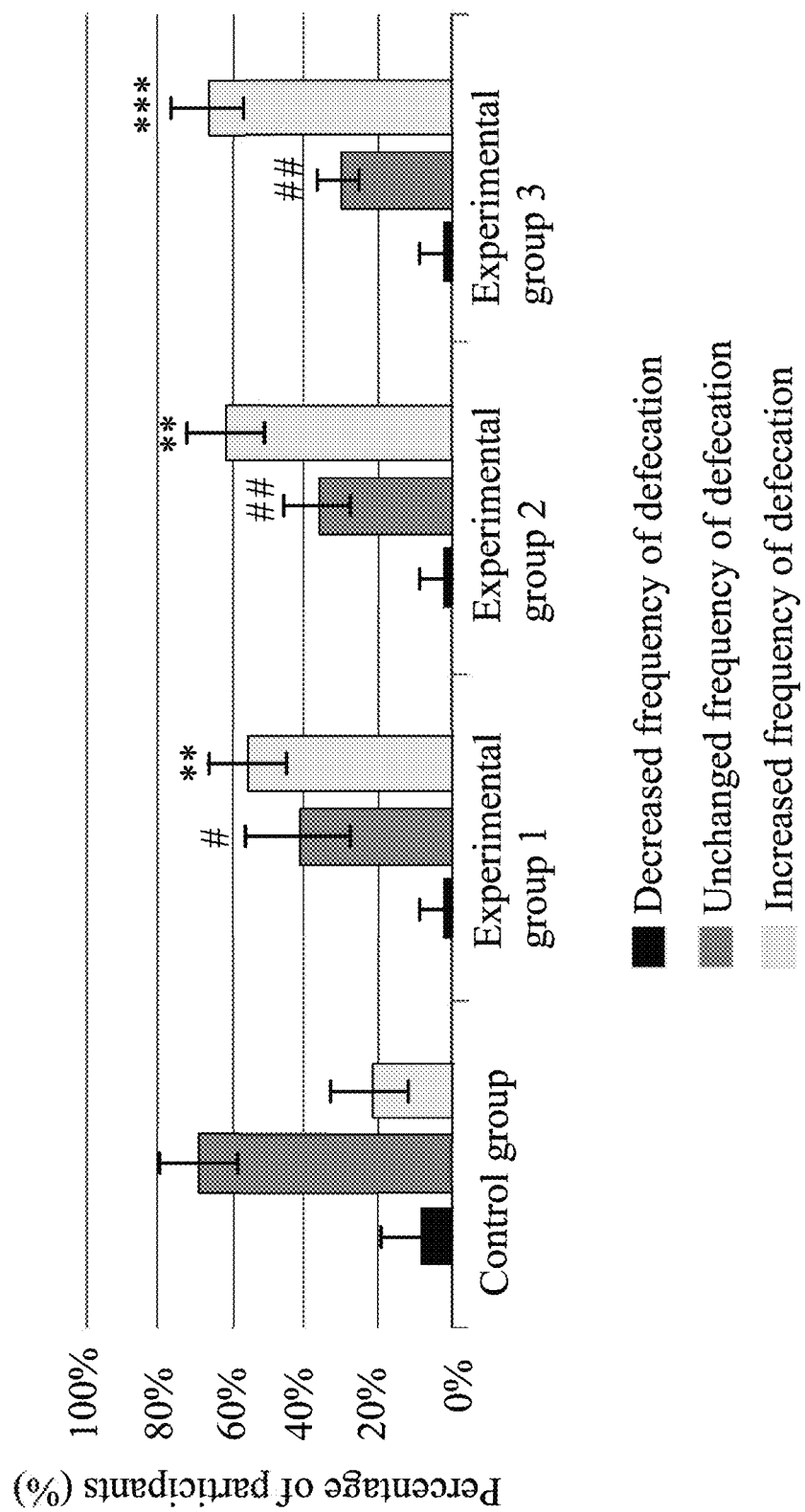

USE OF SPRAY-DRIED POWDER DERIVED FROM LACTIC ACID BACTERIAL STRAINS AND HERBAL EXTRACTS FOR PROMOTING DEFECATION

CROSS-REFERENCE TO RELATED APPLICATION

This application claims priority of Taiwanese Patent Application No. 109121976, filed on Jun. 30, 2020.

FIELD

The present disclosure relates to a composition for promoting defecation. The present disclosure also relates to a method for promoting defecation using the composition.

BACKGROUND

Constipation is usually caused by disorder of peristaltic movement of the intestines, causing the stool being retained within the large intestine for a long time and water in the stool being absorbed until the stool becomes hard and dry, which results in symptoms such as a decrease in frequency and/or volume of bowel movements, difficulty in defecation, abdominal pain, and bloating among others. Moreover, fermentation and decomposition of ingested food by bacteria present in the intestinal tract is prone to produce toxic substances such as aldehydes, ketones, ammonia, etc. These toxic substances, if fail to be discharged normally from the body along with the stool, would be reabsorbed from the intestinal tract to enter into the blood circulatory system, which might cause various metabolic diseases.

The cause of constipation is highly correlated with lifestyle habits, which may include insufficient intake of dietary fiber and fluid, lack of physical activity, pregnancy, psychological stress, anxiety, irregular sleep patterns, among others. In addition, medications such as analgesics, diuretics, anti-depressants, hypotensive agents, etc., cause constipation as a side effect.

Conventional methods commonly used to promote defecation for treating constipation mainly focus on adjusting diet and lifestyle habits, for example, increasing intake of dietary fiber and fluid, having appropriate amount of exercise, etc. However, when such methods fail to achieve the desirable effect, medical substances such as cathartics or fecal softeners are usually combined thereto. Although these medical substances exert an immediate defecation effect, patients taking them might experience severe side effects such as intestinal colic, enteric nervous system disorder, etc. Therefore, those skilled in the art endeavor to find active components from natural sources for promoting defecation.

It has been reported in Jang S. H. et al. (2018), *Korean J. Food & Nutr.*, 31:640-646 that an extract of Chinese herbal medicine (e.g., date plums, cassiae semen seeds, lotus leaf powder, hawthorn, plums, etc.) can be used for treating constipation. However, the Chinese herbal medicine usually requires a long period of time to exert their curative effect. On the other hand, some lactic acid bacteria (e.g., *Lactobacillus*, *Bifidobacterium*, etc.) have been found to provide benefit for patients with constipation, as reported by Eirini Dimidi et al. (2017), *Adv. Nutr.*, 8:484-494. Nevertheless, lactic acid bacteria, which are mainly used to colonize the intestinal tract so as to regulate gut microbiota therein, are susceptible to be destroyed by gastric acid and bile salts after ingestion, causing insufficient amount of the lactic acid bacteria and thus, failure to effectively treat constipation.

Therefore, those skilled in the art still strive to develop an efficient and effective way for promoting defecation and/or treating constipation.

SUMMARY

Therefore, an object of the present disclosure is to provide a composition for promoting defecation which can alleviate at least one of the drawbacks of the prior art.

The composition for promoting defecation includes a cell culture of at least one lactic acid bacterial strain which is substantially free of cells. The at least one lactic acid bacterial strain is selected from the group consisting of *Lactobacillus salivarius* subsp. salicinius AP-32, *Bifidobacterium animalis* subsp. *lactis* CP-9, and *Lactobacillus acidophilus* TYCA06, which are respectively deposited at the Bioresource Collection and Research Center (BCRC) under accession numbers BCRC 910437, BCRC 910645 and BCRC 910813.

Another object of the present disclosure is to provide a method for promoting defecation which can alleviate at least one of the drawbacks of the prior art. The method for promoting defecation includes administering to a subject in need thereof an effective amount of a composition which includes a cell culture of at least one lactic acid bacterial strain that is substantially free of cells. The at least one lactic acid bacterial strain is selected from the group consisting of *Lactobacillus salivarius* subsp. salicinius AP-32, *Bifidobacterium animalis* subsp. *lactis* CP-9, and *Lactobacillus acidophilus* TYCA06, which are respectively deposited at the Bio resource Collection and Research Center (BCRC) under accession numbers BCRC 910437, BCRC 910645 and BCRC 910813.

BRIEF DESCRIPTION OF THE DRAWINGS

Other features and advantages of the present disclosure will become apparent in the following detailed description of the embodiments with reference to the accompanying drawings, of which:

FIG. 1 shows percentages of participants with increased, unchanged and decreased frequency of defecation in each experimental groups compared with those in control group after ingestion of a beverage including a cell culture of the present disclosure, in which the symbols "" and "*" respectively represent $p<0.01$ and $p<0.001$ as compared to the percentage of participants with increased frequency of defecation in the control group, and the symbol "##" and "###" represents $p<0.01$ and $p<0.001$ as compared to the percentage of participants with unchanged frequency of defecation in the control group.

DETAILED DESCRIPTION

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this disclosure belongs. One skilled in the art will recognize many methods and materials similar or equivalent to those described herein, which could be used in the practice of this disclosure. Indeed, this disclosure is in no way limited to the methods and materials described.

In the development of active components that can be used to promote defecation, the applicants unexpectedly found that a cell culture of at least one of specific lactic acid bacterial strains is capable of increasing the frequency of defecation in a subject within a short period of time, and hence is expected to be effective in treating and/or preventing constipation.

Therefore, the present disclosure provides a composition for promoting defecation, including a cell culture of at least one lactic acid bacterial strain which is substantially free of cells. The at least one lactic acid bacterial strain is selected from the group consisting of *Lactobacillus salivarius* subsp. salicinius AP-32, *Bifidobacterium animalis* subsp. *lactis* CP-9, and *Lactobacillus acidophilus* TYCA06, which are respectively deposited at the Bioresource Collection and Research Center (BCRC) under accession numbers BCRC 910437, BCRC 910645 and BCRC 910813.

As used herein, the term "defecation" refers to the final act of digestion, by which solid, semisolid or liquid waste materials that remains after food ingestion are eliminated from the digestive or gastrointestinal tract of a subject via the anus.

As used herein, the term "promoting defecation" means facilitating, stimulating, assisting, helping, enhancing and/or easing defecation by, e.g., increasing the frequency and/or efficacy of defecation or shortening the time from food intake to defecation.

As used herein, the term "treating" or "treatment" means preventing, reducing, alleviating, ameliorating, relieving, or controlling the severity of constipation, or lowering, stopping or reversing the progression of the severity of constipation, so as to partially or entirely eliminate constipation.

As used herein, the term "preventing" or "prevention" means eliminating or reducing the incidence of constipation in a subject not yet been diagnosed with constipation, or slowing, delaying, controlling, or decreasing the likelihood or probability of constipation in the subject.

As used herein, the term "subject" refers to any animal of interest, such as humans, monkeys, cows, sheep, horses, pigs, goats, dogs, cats, mice, and rats. In certain embodiments, the subject is a human.

According to this disclosure, the cell culture substantially free of cells is prepared by culturing the abovementioned at least one lactic acid bacterial strain in a liquid culture suitable for growth and/or proliferation thereof, and then subjecting the resultant cultured product to a separation process to remove bacterial cells therefrom, thereby obtaining the cell culture free of the lactic acid bacterial strain.

As used herein, the term "culturing" can be used interchangeably with other terms such as "fermentation" and "cultivation".

In certain embodiments, the culture medium is in a liquid form (i.e., a liquid medium). Example of the liquid medium suitable for culturing the lactic acid bacterial strain may include, but is not limited to, MRS (De Man, Rogosa and Sharpe) broth.

In a case of the liquid medium being used for culturing the lactic acid bacterial strain, any conventional separation process such as filtering or sedimentary methodologies (e.g., centrifugation, concentration, etc.) may be performed to remove bacterial cells from the cultured product, and the resultant liquid portion (such as filtrate or supernatant) which may include secreted metabolites from the cultured lactic acid bacterial strain is collected as the cell culture of this disclosure.

According to the present disclosure, the liquid medium suitable for culturing the lactic acid bacterial strain may include a carbon source selected from the group consisting of glucose, fructose, lactose, sucrose, maltose, galactose, mannose, trehalose, starch, molasses, potato starch, corn starch, malt extract, maltodextrin, and combinations thereof.

According to this disclosure, the liquid medium suitable for culturing the lactic acid bacterial strain may include a nitrogen source selected from the group consisting of ammonium sulfate ($[NH_4]_2SO_4$), ammonium phosphate ($[NH_4]_3PO_4$), ammonium nitrate ($NH_4NO_3$), ammonium. chloride ($NH_4Cl$), casamino acid, urea, peptone, polypeptone, tryptone, meat extract, yeast extract, yeast powder, cow's milk, milk powder, soy products (e.g., soybean flour), whey, and combinations thereof.

The procedures and conditions for culturing the lactic acid bacterial strain may be adjusted according to practical requirements. In this regard, those skilled in the art may refer to journal articles, e.g., Hsieh P. S. et al. (2013), *New Microbiol.*, 36:167-179.

In certain embodiments, the lactic acid bacterial strain is cultured at a temperature ranging from 30° C. to 40° C. for a time period ranging from 12 hours to 24 hours.

As used herein, the term "substantially free of" means that the cell culture lacks a significant amount of a specified component (i.e., lactic acid bacterial cells). In certain embodiments, the amount of the lactic acid bacterial cells does not have a measurable effect on the properties of the cell culture. In other embodiments, the composition is completely free of the bacterial cells.

According to the present disclosure, after the separation process, a drying process may be performed using techniques well-known to those skilled in the art, so as to obtain a product in a powder form. Examples of the drying process may include, but are not limited to, lyophilization treatment, low temperature spray-drying treatment, vacuum evaporation treatment, and combinations thereof.

According to this disclosure, the composition may further include a herbal extract. Examples of the herbal extract may include, but are not limited to, a date plum extract, a semen cassiae extract, a lotus leaf extract, and combinations thereof.

In certain embodiments, the herbal extract includes the date plum extract, the semen cassiae extract, and the lotus leaf extract.

In certain embodiments, the cell culture of at least one lactic acid bacterial strain is present in an amount ranging from 1 wt % to 10 wt % based on a total weight of the composition including the herbal extract.

In certain embodiments, the date plum extract is present in an amount ranging from 1 wt % to 20 wt % based on a total weight of the composition. In other embodiments, the date plum extract is present in an amount ranging from 1 wt % to 10 wt % based on a total weight of the composition.

In certain embodiments, the semen cassiae extract is present in an amount ranging from 0.1 wt % to 10 wt % based on a total weight of the composition. In other embodiments, the semen cassiae extract is present in an amount ranging from 0.1 wt % to 1 wt % based on a total weight of the composition.

In certain embodiments, the lotus leaf extract is present in an amount ranging from 0.1 wt % to 10 wt % based on a total weight of the composition. In other embodiments, the lotus leaf extract is present in an amount ranging from 0.1 wt % to 1 wt % based on a total weight of the composition.

The date plum extract, the semen cassiae extract, and the lotus leaf extract may be prepared using techniques well-known to those skilled in the art, and independently using an extraction solvent selected from the group consisting of water, methanol, ethanol, ethyl acetate, and combinations thereof. In certain embodiments, the date plum extract is prepared by extracting date plum fruits using water. In certain embodiments, the semen cassiae extract is prepared by extracting semen cassiae plants seeds using water. In certain embodiments, the lotus leaf extract is prepared by extracting lotus leaf using water.

It should be noted that the procedures and conditions for preparing the herbal extract may be varied based on the preparation technique and amount of the herbs, so as to obtain an optimal amount of the herbal extract. Such procedures and conditions can be routinely optimized by those skilled in the art.

According to the present disclosure, the composition may further include an additional plant extract. Examples of the additional plant extract may include, but are not limited to, a plum extract, a hawthorn extract, a kiwi extract, a sweet potato extract, an apple extract, and combinations thereof.

In certain embodiments, the composition of this disclosure is formulated as a food product using a standard technique well known to one of ordinary skill in the art. For example, the composition may be directly added to an edible material or may be used to prepare an intermediate composition (e.g., a premix) suitable to be subsequently added to the edible material.

The food product of the present disclosure may further include a food additive selected from the group consisting of sorbitol, lactitol, lactose, lactic acid, acesulfame potassium, sucralose, and combinations thereof.

As used herein, the term "food product" refers to any article or substance that can be ingested by a subject into the body thereof. Examples of the food product may include, but are not limited to, milk powder, fermented milk, yogurt, butter, beverages (e.g., tea, coffee, etc.), functional beverages, flour product, baked foods, confectionery, candies, fermented foods, animal feeds, health foods, and dietary supplements.

In certain embodiments, the composition according to this disclosure is formulated as a pharmaceutical preparation. The pharmaceutical preparation may further include a pharmaceutically acceptable carrier, and may be made into a dosage form suitable for oral administration using technology well-known to those skilled in the art. Examples of the oral dosage form include, but are not limited to, sterile powder, tablets, troches, lozenges, pellets, capsules, dispersible powder, granule, solutions, suspensions, emulsions, syrup, elixirs, slurry, and the like.

Examples of the pharmaceutically acceptable carrier may include, but are not limited to, solvents, buffers, emulsifiers, suspending agents, decomposers, disintegrating agents, dispersing agents, binding agents, excipients, stabilizing agents, chelating agents, diluents, gelling agents, preservatives, wetting agents, lubricants, absorption delaying agents, liposomes, and the like. The choice and amount of the pharmaceutically acceptable carrier are within the expertise of those skilled in the art.

Since the composition of the present disclosure has been verified through in vivo test to effectively increase the frequency of defecation in human subjects, the present disclosure also provides a method for promoting defecation, including administering to a subject in need thereof an effective amount of the abovementioned composition. By virtue of promoting defecation, the composition is also expected to have an effect of treating and/or preventing constipation in the subject.

As used herein, the term "administering" or "administration" means introducing, providing or delivering the abovementioned composition to a subject showing condition(s) or symptom(s) of constipation by any suitable routes to perform its intended function.

The dose and frequency of administration of the composition may vary depending on the following factors: the severity of the illness or disorder to be treated, routes of administration, and age, physical condition and response of the subject to be treated. In general, the composition may be administered in a single dose or in several doses.

The present disclosure will be further described by way of the following examples. However, it should be understood that the following examples are intended solely for the purpose of illustration and should not be construed as limiting the present disclosure in practice.

EXAMPLES

General Experimental Materials:
1. Lactic Acid Bacterial (LAB) Strains
A. *Lactobacillus salivarius* subsp. salicinius AP-32

*Lactobacillus salivarius* subsp. salicinius AP-32, which is disclosed in the applicants' previous Taiwanese Invention Patent Publication No. 1542353, has been deposited at the Biosource Collection and Research Center (BCRC) of the Food Industry Research and Development Institute (FIRDI) (No. 331, Shih-Pin Rd., Hsinchu City 300, Taiwan) under accession number BCRC 910437 since Jul. 30, 2009.

B. *Bifidobacterium animalis* Subsp. *Lactis* CP-9

*Bifidobacterium animalis* subsp. *lactis* CP-9, which is disclosed in the applicants' previous Taiwanese Invention Patent Publication No. 1572713, has been deposited at the BCRC of the FIRDI under accession number BCRC 910645 since Aug. 21, 2014.

C. *Lactobacillus acidophilus* TYCA06

*Lactobacillus acidophilus* TYCA06, which is disclosed in the applicants' previous Taiwanese Invention Patent Publication No. 1701034, has been deposited at the BCRC of the FIRDI under accession number BCRC 910813 since Jan. 18, 2018.

Example 1. Preparation of Cell Culture of Lactic Acid Bacterial (LAB) Strain of the Present Disclosure First, a respective one of the three LAB strains as described in the section entitled "1. Lactic acid bacterial (LAB) strains" of the General Experimental Materials was inoculated into 5 L of a MRS (De Man, Rogosa and Sharpe) medium purchased from Creative LifeSciences Co., Ltd., Taiwan, and then cultured at a temperature ranging from 30° C. to 40° C. for 12 to 24 hours to obtain a respective inoculum. Next, the respective inoculum was poured into 5 L of a fresh MRS medium to be cultured at 30° C. to 40° C. for 12 to 24 hours so as to obtain a LAB strain cultured product. After that, each of the LAB strain cultured products was subjected to centrifugation, and the resultant supernatant (i.e., liquid portion) which is substantially free of bacterial cells was collected and then subjected to sterilization by heating, followed by a spray-drying treatment, so as to obtain a respective one of the following: a spray-dried powder of AP-32 cell culture, a spray-dried powder of CP-9 cell culture, and a spray-dried powder of TYCA06 cell culture.

In a preliminary test, the spray-dried powders of the cell cultures of the LAB strains were individually mixed with maltodextrin, and then manufactured into a respective one of capsules (each of which may contain the spray-dried powder of the cell culture in an amount ranging from 30 wt % to 50 wt % [e.g., 200 mg in this example] based on 100 wt % of the capsule) for oral administration to 15 test subjects in an administration frequency of 3 capsules per day for 1 month. Before the administration and on the last week of administration, frequency of defecation (i.e., the number of times of defecation) for each subject was recorded. The results show that as compared to the frequency of defecation in the subjects before administration of the capsules, the subjects have an increased frequency of defecation after administration of the capsules, which contain the respective one of spray-dried powders of cell cultures of this disclosure (data not shown), indicating that the cell culture of each of *Lactobacillus salivarius* subsp. salicinius AP-32, *Bifidobacterium animalis* subsp. *lactis* CP-9, and *Lactobacillus acidophilus* TYCA06 has the potential for promoting defecation. Therefore, these cell cultures were subjected to the following experiments.

Example 2. Evaluation for the Effect of Cell Culture of Each LAB Strain on Promoting Defecation Experimental Materials:
A. Preparation of Beverages Including Cell Culture of Each LAB Strain 2 wt % of a respective one of the spray-dried powder of AP-32 cell culture, the spray-dried powder of CP-9 cell culture, and the spray-dried powder of TYCA06 cell culture as prepared in Example 1 was mixed with herbal extracts and food additives so as to obtain a AP-32 beverage, a CP-9 beverage and a TYCA06 beverage (hereinafter abbreviated as beverages 1, 2, and 3, respectively). The source and amount of each ingredient in these three beverages are shown in Table 1 below.

TABLE 1

| Ingredients | | Source | Amount (wt %) |
|---|---|---|---|
| Cell culture | | — | 2% |
| Herbal extracts | Date plum extract | Fengjia Biotechnology Co., Ltd., Taiwan | 1-20 |
| | Semen cassiae extract | Champion Co., Ltd., Taiwan | 0.1-10 |
| | Lotus leaf extract | Biotrue Co., Ltd., Taiwan | 0.1-10 |
| Food additives | Sorbitol | Sheng Yuan Food Industrial Co., Ltd., Taiwan | 5-20 |
| | Lactitol | Sei Cheng Biotechnology Co., Ltd., Taiwan | 5-20 |
| | Lactose | | 1-5 |
| | Lactic acid | Chien Cheng Trading Co., Ltd., Taiwan | 0.1-1 |
| | Acesulfame potassium | Shinemate Co., Ltd., Taiwan | 0.001-0.005 |
| | Sucralose | Heng Yi Trading Co., Ltd., Taiwan | 0.001-0.005 |
| | Potassium sorbate | Sheng Lin Industrial Co., Ltd., Taiwan | 0.1-0.5 |

The balance is deionized water.

In addition, a control beverage having a composition similar to the abovementioned beverages 1, 2, and 3 except for exclusion of the cell culture, is also formulated for comparison purpose.

Experimental Subjects:

Participants of the following experiments are employees of Glac Biotech Co., Ltd., Taiwan, and include 13 men and 23 women aged between 25 and 50 years old.

The participants are selected based on the following exclusion criteria: pregnant women, breastfeeding women, smokers, and those who abuse or are addicted to drugs and/or alcohols.

Experimental Procedures:

First, the 36 participants were randomly divided into 4 groups, i.e., experimental groups 1, 2, and 3 and a control group, in which the number of participants in each group is 9. The frequency of defecation within the last 24 hours for each participants were recorded prior to being subjected to the following experiments. Then, the participants in the experimental groups 1, 2, and 3, and the control group respectively ingest 50 mL of the beverages 1, 2, and 3, and the control beverage, and the frequency of defecation for each participants were recorded within 24 hours thereafter.

Each of the experimental groups 1, 2, and 3 and the control group were subjected to the abovementioned experiment for three rounds with a time gap of 1 week between each round of experiments, and each participant was assigned to different groups each round so as to prevent health differences of each participants from adversely affecting the overall result.

Changes in the number of times of defecation recorded before and after ingesting the beverage for the participants in each group were analyzed, so as to determine the percentages of participants with increased frequency of defecation, unchanged frequency of defecation, and with decreased frequency of defecation for each group. These experimental data are expressed as mean±standard error of the mean (SEM) and were analyzed using two-tailed Student's t-test so as to determine the difference between these groups, where p-value<0.05 was considered to be statistically significant.

Results:

FIG. 1 shows percentages of the participants having the increased, unchanged, and decreased frequency of defecation in each group after ingestion of the beverages. As shown in FIG. 1, for each group, the percentage of the participants having an increased frequency of defecation is higher than that having a decreased frequency of defecation. In addition, as compared to the control group, the percentage of the participants having unchanged frequency of defecation in each of the experimental groups 1, 2, and 3 was significantly lower, while the percentage of the participants having an increased frequency of defecation in each of the experimental groups 1, 2, and 3 was significantly higher, in which the experimental group 3 exhibits the highest percentage of participants thereamong. These results suggest that the cell culture of a respective one of *Lactobacillus salivarius* subsp. salicinius AP-32, *Bifidobacterium animalis* subsp. *lactis* CP-9, and *Lactobacillus acidophilus* TYCA06 shows a significantly improved effect for increasing the frequency of defecation, even after one day of ingestion of the cell culture. As such, the abovementioned cell culture of at least one lactic acid bacterial strain of this disclosure, either alone or in combination with the herbal extract (such as the date plum extract, the semen cassiae extract, and the lotus leaf extract), is expected to be useful to effectively promote defecation, thereby being capable of treating constipation.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A composition for promoting defecation, comprising:
a spray-dried powder TYCA06 derived from a cell-free culture of *Lactobacillus acidophilus* TYCA06; and
an herbal extract including a date plum extract, a semen cassiae extract, and a lotus leaf extract,
wherein based on a total weight of said composition, said spray-dried powder of TYCA06 derived from said cell-free culture of *Lactobacillus acidophilus* TYCA06 is present in an amount ranging from 1 wt % to 10 wt %, said date plum extract is present in an amount ranging from 1 wt % to 20 wt %, said semen cassiae extract is present in an amount ranging from 0.1 wt % to 10 wt %, and said lotus leaf extract is present in an amount ranging from 0.1 wt % to 10 wt %.

2. The composition as claimed in claim 1, wherein said composition is formulated as a food product.

3. The composition as claimed in claim 1, wherein said composition is formulated as a pharmaceutical preparation.

4. A method for promoting defecation, comprising administering to a subject in need thereof an effective amount of a composition which includes a spray-dried powder of TYCA06 derived from a cell-free culture of *Lactobacillus acidophilus* TYCA06, and an herbal extract which includes a date plum extract, a semen cassiae extract, and a lotus leaf extract,
wherein based on a total weight of the composition, the spray-dried powder of TYCA06 derived from the cell-free culture of *Lactobacillus acidophilus* TYCA06 is present in an amount ranging from 1 wt % to 10 wt %, the date plum extract is present in an amount ranging from 1 wt % to 20 wt %, the semen cassiae extract is present in an amount ranging from 0.1 wt % to 10 wt %, and the lotus leaf extract is present in an amount ranging from 0.1 wt % to 10 wt %.

5. The method as claimed in claim 4, wherein the composition is formulated as a food product.

6. The method as claimed in claim 4, wherein the composition is formulated as a pharmaceutical preparation.

7. The method as claimed in claim 4, wherein the composition is orally administered.

8. The composition as claimed in claim 1, further comprising a spray-dried powder of AP-32 derived from a cell-free culture of *Lactobacillus salivarius* subsp. salicinius AP-32.

9. The composition as claimed in claim 1, further comprising a spray-dried powder of CP-9 derived from a cell-free culture of *Bifidobacterium animalis* subsp. *lactis* CP-9.

* * * * *